United States Patent [19]

Boigegrain et al.

[11] Patent Number: 5,081,119
[45] Date of Patent: Jan. 14, 1992

[54] USE OF 5-ALKYLPYRIDAZINE DERIVATIVES AS DRUGS ACTIVE ON THE CHOLINERGIC SYSTEM

[75] Inventors: Robert Boigegrain, Clapiers; Camille G. Wermuth, Strasbourg; Paul Worms, St Gely Du Fesc, all of France

[73] Assignee: Sanofi, Paris, France

[21] Appl. No.: 475,490

[22] Filed: Feb. 7, 1990

[30] Foreign Application Priority Data

Feb. 7, 1989 [FR] France .................. 89 01546

[51] Int. Cl.$^5$ .................. A61K 31/50; A61K 31/535
[52] U.S. Cl. .................. 514/231.5; 514/247
[58] Field of Search .................. 514/231.5, 247

[56] References Cited

U.S. PATENT DOCUMENTS 4,508,720  4/1985  Jean-Paul Kan et al. .......... 514/247

FOREIGN PATENT DOCUMENTS 2141697  1/1973  France .
2510997  2/1984  France .
2510998  1/1986  France .

OTHER PUBLICATIONS

Van der Brempt, et al., "Structure Analysis of Minaprine Analogs: 3-Morpholinium Ethylamin-5-Methyl-6-Phenylpyridazinium Oxalate, Oxalic Acid" *Chemical Abstracts* 103:552, No. 204113u (1985).

Hammer et al., "Pirenzepine Distinguishes Between Different Subclasses of Muscarinic Receptors," *Nature* 283:90-92 (1980).

Hulme et al., "The Binding of Antagonists to Brain Muscarinic Receptors," *Molecular Pharmacology* 14:737-750 (1978).

Watson et al., "[$^3$H]Pirenzepine Selectively Identifies a High Affinity Population of Muscarinic Cholinergic Receptors in the Rate Cerebral Cortex$^1$," *Life Science* 31:2019-2023 (1982).

Worms et al., "Antagonism by Cholinomimetic Drugs of the Turning Induced by Intrastriatal Pirenzepine in Mice," *Psychopharmacology* 93:489-493 (1987).

*Primary Examiner*—Stanley J. Friedman
*Attorney, Agent, or Firm*—Foley & Lardner

[57] ABSTRACT

The invention relates to the use of 5-alkylpyridazine derivatives of the formula

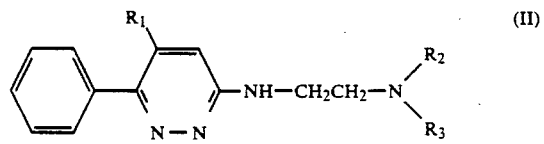

(II)

in which $R_1$ is a $C_1$-$C_4$ alkyl group or a phenyl group and $R_2$ and $R_3$ independently are a $C_1$-$C_4$ alkyl group, or $R_2$ and $R_3$, taken with the nitrogen atom to which they are bonded, form a morpholino group, or one of their pharmaceutically acceptable salts, for the preparation of pharmaceutical compositions for combating pathological conditions associated with a cortical cholinergic deficiency, especially for the treatment of degenerative syndromes associated with senescence.

9 Claims, No Drawings

USE OF 5-ALKYLPYRIDAZINE DERIVATIVES AS DRUGS ACTIVE ON THE CHOLINERGIC SYSTEM

Pyridazine derivatives have been proposed as drugs for many years.

In a large number of cases, these are substances which are active on the cardiovascular system and have in particular a hypotensive or vasodilative effect; in other cases, an antiinflammatory and analgesic action has been mentioned for pyridazine derivatives.

Finally, French patents 2 141 697, 2 510 997 and 2 510 998 disclose pyridazine derivatives which are variously substituted on the pyridazine ring and all carry, in the 3-position, an amino substituent of the type

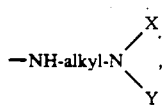

in which X and Y independently are hydrogen or an alkyl group or form, with the nitrogen atom to which they are bonded, a heterocycle such as morpholine.

All these compounds are active on the central nervous system as antidepressants.

More particularly, French patent n 2 510 998 describes a family of pyridazine derivatives which includes a 5-alkylpyridazine derivative, namely 3-(2-morpholinoethylamino)-5-methyl-6-phenylpyridazine (I), among its members.

This compound has antidepressant properties of moderate intensity. Subsequent studies have shown that it also possesses valuable properties as a ligand for the cholinergic receptors.

In mammals, there are two subclasses of muscarinic cholinergic receptors: the $M_1$ and $M_2$ receptors.

The $M_1$-type receptors are concentrated in certain areas of the brain, such as the hippocampus, the cerebral cortex and the striatum, and in the sympathetic ganglia. These binding sites can be selectively labeled with [$^3$H]-pirenzepine. The $M_2$-type receptors are predominant in the heart and ileum and can be labeled with [$^3$H]-N-methylscopolamine.

Senile dementia, and especially dementia of the Alzheimer type, are serious complaints whose frequency is tending to increase with the longevity of the population.

The studies undertaken by different authors have demonstrated the existence, in these diseases, of a specific deficiency of cortical cholinergic markers, causing serious disorders of the higher functions.

The results obtained by using muscarinic agonists for the treatment of senile dementia have proved encouraging. However, there are only a small number of muscarinic agonists in existence and they have been found difficult to manage in man.

Consequently, the search for postsynaptic muscarinic agonists as a treatment for senile dementia is currently regarded as highly desirable.

The value of having selective central muscarinic agonists for overcoming the cholinergic deficiency in Alzheimer's disease has been mentioned especially in ISI Atlas of Science: Pharmacology (1987), p. 98 to 100.

The present invention therefore relates to the use of the compound (I) and related compounds as selective central muscarinic agonists which can be used as drugs for the treatment of diseases associated with a central cholinergic deficiency, and especially for the treatment of senile dementia.

These compounds have the general formula

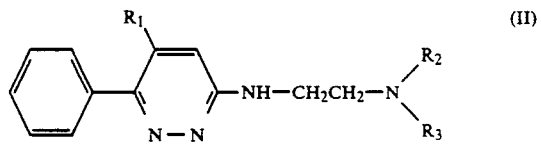

in which $R_1$ is a $C_1$-$C_4$ alkyl group or a phenyl group; and $R_2$ and $R_3$ independently are a $C_1$-$C_4$ alkyl group, or $R_2$ and $R_3$, taken with the nitrogen atom to which they are bonded, form a morpholino group.

The invention also includes the salts which the compounds of formula (II) are capable of forming with pharmaceutically acceptable acids.

The compounds of formula II wherein $R_1$ is a $C_2$-$C_4$ alkyl group and $R_2$ and $R_3$ are as hereinabove defined are new as well as their pharmaceutically acceptable salts and therefore represent a further aspect of the present invention. Among these new compounds, the compounds wherein $R_1$ is —$CH_2$—$CH_3$ or —$CH_2$—$CH_2$—$CH_3$ are particularly preferred.

The compounds of formula (II) can be prepared by reacting an amine

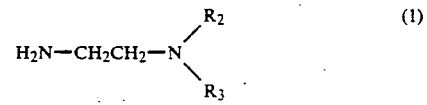

with the chlorine derivative

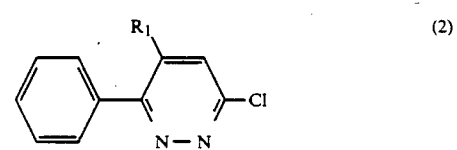

The reaction is performed by heating the chlorine derivative (2) with a large excess of amine (1) at between 100° and 150° C., if appropriate in the presence of ammonium chloride.

The reaction is carried out without a solvent or in an inert solvent such as n-butanol.

The chlorine derivatives (2) can be prepared from a phenyl ketone (3) according to the following reaction scheme:

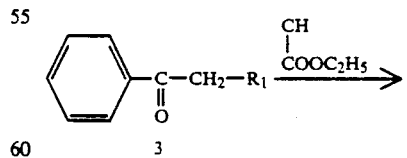

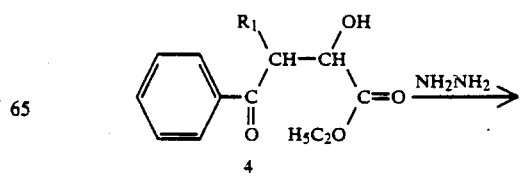

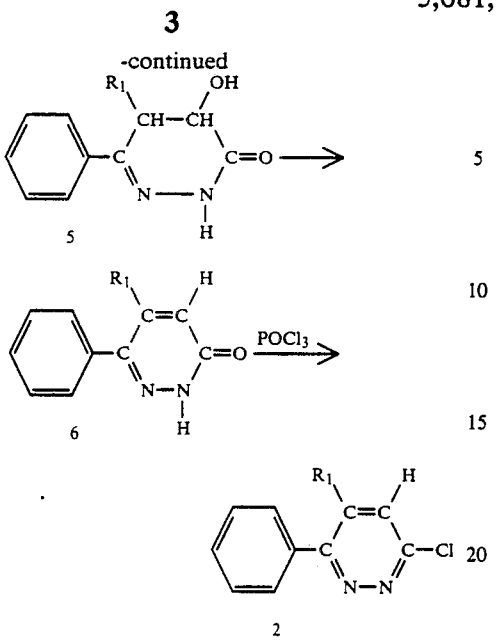

Heating the ketone 3 with ethyl glyoxylate at a temperature of between 80° and 140° C. gives the hydroxyketoester 4. The crude reaction mixture is then taken up in an inert solvent such as n-butanol, and hydrazine hydrate is added. Refluxing for 24 hours gives the hydroxypyridazinone 5, which, when heated in an acid medium, yields the 2H-pyridazin-3-one 6 by dehydration.

Heating the latter with excess phosphorus oxychloride gives the 3-chloropyridazine 2. The reaction is carried out without a solvent or in the presence of an inert solvent such as acetonitrile.

In all cases, the products (II) isolated in the form of the base can be converted to salts by reaction with an equimolecular amount of a pharmaceutically acceptable acid in a suitable solvent.

The following Examples illustrate the preparation of the compounds of formula (II).

EXAMPLE 1

3-(2-Morpholinoethylamino)-5-methyl-6-phenylpyridazine dioxalate (CM 30316)

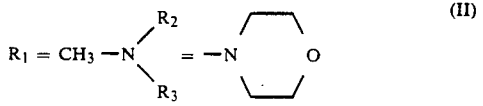

A) 3-Chloro-5-methyl-6-phenylpyridazine

1. Ethyl 2-hydroxy-3-methyl-4-phenyl-4-oxobutyrate

A mixture of 13.4 g of propiophenone and 15.3 g of ethyl glyoxylate is heated at 135° C. for 5 hours.

The resulting product is used as such for the next operation.

2. 5-Methyl-6-phenyl-2H-pyridazin-3-one

The crude product obtained above is dissolved in 150 ml of n-butanol, 9.44 ml of hydrazine hydrate are then added and the mixture is refluxed for 24 hours.

Part of the n-butanol is distilled at ordinary pressure in order to remove the water formed in the reaction as an azeotrope. The mixture is then concentrated to dryness under vacuum. The residue is taken up in a mixture of 100 ml of acetic acid and 10 ml of concentrated hydrochloric acid. The mixture is heated at 100° C. for 4 hours. The solution is poured into cold water and left to crystallize. The solid is filtered off and dried.

Weight: 11.6 g M.p.: 218° C.

3. 3-Chloro-5-methyl-6-phenylpyridazine 50 ml of phosphorus oxychloride are added to 12 g of the pyridazinone obtained above and the mixture is heated at 80° C. for 4 hours.

The mixture is poured slowly on to ice and rendered alkaline with a 20% solution of sodium hydroxide.

The precipitate is filtered off, washed copiously with water and recrystallized from isopropanol.

9.9 g of the expected product are obtained.

M.p.: 122° C.

B) CM 30316

A mixture of 8 g of the chlorine derivative obtained above and 10 g of 2-morpholinoethylamine in 80 ml of n-butanol is refluxed for 12 hours.

The hot solution is poured into 200 ml of water and the precipitate is filtered off and washed with a small amount of ether. The aqueous phase is separated off and extracted with ether. The ether extracts are combined and extracted with a 1N solution of sulfuric acid.

The acid aqueous phase is separated off and rendered alkaline with a 10% solution of sodium carbonate. It is extracted with ethyl acetate and the solution is dried over sodium sulfate and evaporated to dryness under vacuum.

The base obtained is dissolved in isopropyl ether and 2 equivalents of oxalic acid are added. The mixture is heated at the boil until the oxalic acid has dissolved. The dioxalate crystallizes on cooling. It is filtered off and recrystallized from the same solvent.

Weight: 6 g M.p.: 182°–183° C.

EXAMPLES 2 TO 7

A) The 3-chloropyridazines collated in the Table below are obtained by following the procedure of Example 1A, but varying the starting ketone:

TABLE 1

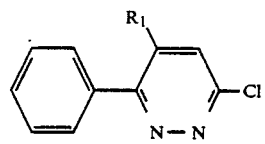

| $R_1$ | Physical constants |
|---|---|
| —CH$_2$CH$_3$ | M.p.: 70° C. |
| —CH$_2$CH$_2$CH$_3$ | M.p.: 60° C. |
| —C$_6$H$_5$ | — |

The compounds (II) collated in Table 2 are obtained from these chlorine derivatives and that of Example 1A by following the technique of Example 1B, varying the amines used.

TABLE 2

Structure:

R$_1$ substituent on a phenyl-pyridazine-NHCH$_2$CH$_2$N(R$_2$)(R$_3$) scaffold, where the NR$_2$R$_3$ group forms the indicated cyclic/acyclic amine.

| Ex. | ref. n° | R$_1$ | —N(R$_2$)(R$_3$) | Salt M.p.: °C. |
|---|---|---|---|---|
| 2 | SR 96169 A | —CH$_2$CH$_3$ | —N(morpholino) | Monooxalate 1.5H$_2$O: 195 |
| 3 | SR 96186 A | —CH$_2$CH$_2$CH$_3$ | " | Monooxalate: 195 |
| 4 | SR 96150 A | —CH$_3$ | —N(CH$_2$CH$_3$)$_2$ | Dioxalate: 152 |
| 5 | SR 96180 A | —CH$_2$CH$_3$ | " | Dioxalate: 106 |
| 6 | SR 96187 A | —CH$_2$CH$_2$CH$_3$ | " | Dioxalate: 143 |
| 7 | CM 30365 | —C$_6$H$_5$ | —N(morpholino) | Dichlorohydrate: 235 |

The compounds of formula (II) were studied for their therapeutic properties and especially for their affinity for the muscarinic cholinergic receptors.

In vitro, we studied the interaction of the products (II) with tritiated pirenzepine and tritiated N-methylscopolamine bound with a high affinity to membranes of rat hippocampus and membranes of smooth muscle of guinea-pig ileum, respectively.

Methodologies

A) Test for affinity for the M$_1$-type muscarinic cholinergic receptor

The interaction of molecules with the M$_1$-type muscarinic receptors was studied by in vitro measurement, on a homogenate of rat hippocampus, of the displacement of tritiated pirenzepine ([$^3$H]-PZ) from its specific binding sites. Aliquots (100 μl) of a 5% (w/v) homogenate of rat hippocampus in an Na$_2$HPO$_4$ buffer (50 mM, pH 7.40) are incubated for 2 h at 4° C. in the presence of [$^3$H]-PZ (76 Ci/mmol; final concentration: 1 nM) and increasing concentrations of test products. The final volume is 2 ml. The reaction is stopped by centrifugation for 10 min at 50,000×g. After decantation and washing of the residues, the bound radioactivity is counted by liquid scintillation. The non-specific binding is determined in the presence of 10 μmol/l of atropine sulfate. The 50% inhibitory concentration (IC$_{50}$) is determined graphically (Ref.: Watson J. D., Roeskoe W. R. and Yamamura H. I., Life Sci., 31, 2019–2029, 1982).

B) Test for affinity for the M$_2$-type muscarinic cholinergic receptor.

The interaction with the M$_2$-type muscarinic receptors was studied by in vitro measurement, on a homogenate of smooth muscle of guinea-pig ileum, of the displacement of tritiated N-methylscopolamine ([$^3$H]-NMS) from its specific binding sites. Aliquots (50 μl) of a 0.625% (w/v) homogenate of smooth guinea-pig muscle in HEPES buffer (20 mM) containing NaCl (100 mM) and MgCl$_2$ (10 mM) (final pH: 7.5) are incubated for 20 min at 30° C. in the presence of [$^3$H]-NMS (85 Ci/mmol; final concentration: 0.3 nM) and increasing concentrations of test products. The final volume is 1 ml. The reaction is stopped by centrifugation for 5 min at 15,000×g. The non-specific binding is determined in the presence of 10 μmol-l of atropine sulfate (Ref.: Hammer R., Berrie C. P., Birdsall N. I. M., Burgen A. S. V. and Hulme E. C., Nature, 283, 90–92, 1980; Hulme E. C., Birdsall N. I. M., Burgen A. S. V. and Mettha P., Mol. Pharmacol., 14, 737–750, 1978).

Results

Table 3 indicates the affinities of the products of the invention for the M$_1$ and M$_2$ receptors. The results are expressed as 50 percent inhibitory concentrations (IC$_{50}$), i.e. the concentration (in μM) which causes a 50% inhibition of the binding of the tritiated ligand to the membrane receptors. The IC$_{50}$ for displacement of $^3$H-pirenzepine represents the affinity for the M$_1$ receptor; the IC$_{50}$ for displacement of $^3$H-NMS represents the affinity for the M$_2$ receptor.

The Table also indicates, in the 3rd column, the ratio r of the M$_2$ and M$_1$ IC$_{50}$ values, which expresses the selectivity of the products towards the M$_1$ receptor.

TABLE 3

| Product n° | $^3$H-PZ (M$_1$) IC$_{50}$ μM | $^3$H-NMS (M$_2$) IC$_{50}$ μM | r = M$_2$/M$_1$ |
|---|---|---|---|
| CM 30316 | 0.55 | 100 | 182 |
| SR 96169 A | 3.7 | 30 | 8 |
| SR 96186 A | 0.6 | 18 | 30 |
| SR 96150 A | 0.06 | 2.8 | 47 |
| SR 96180 A | 0.07 | 1 | 14 |
| SR 96187 A | 0.4 | 3.5 | 9 |

These results show that the compounds according to the invention have a strong affinity for the muscarinic cholinergic receptors with a marked specificity for the M$_1$-type central receptors.

The compounds of formula (II) were also subjected to an in vivo study.

Pirenzepine (PZ) is a specific antagonist of ligands for the M$_1$ central muscarinic cholinergic receptors. The intrastriatal injection of PZ into mice induces rotational behavior. The antagonism of this behavior by the test products was studied.

The products according to the invention are administered orally after solubilization in distilled water or suspension in a 5% solution of gum arabic. The control animals receive an injection of the pure solvent under the same conditions.

The animals used are female mice (Swiss, DC 1, Charles River, France) with a body weight of between 25 and 30 grams.

Pirenzepine is dissolved in a phosphate buffer; the pH of the solution is 6.

The test products or their solvents are administered orally in a volume of 0.4 ml per 20 g of body weight, 4 hours before a direct injection of pirenzepine at a dose of 1 μg of product in 1 μl of solvent into the right striatum of the mouse, according to the method described by P. Worms et al. in Psychopharmacology 1987, 93, 489–493.

The number of contralateral rotations (rotations in the opposite direction to the side injected) was counted for three 2-minute periods after the injection of pirenzepine: minutes 2 to 4, 8 to 10 and 13 to 15. Each treatment involves 10 animals per dose. For each treatment, the total number of rotations and the percentage antagonism compared with the control group are calculated.

The results obtained with the products of formula (II) administered orally at a dose of 3 mg/kg of body weight are collated in Table 4.

TABLE 4

| Product n° | % inhibition of rotations PZ 3 mg/kg p.o. |
|---|---|
| CM 30316 | −20%* |
| SR 96169 A | −46%** |
| SR 96186 A | −41%** |
| SR 96150 A | −49%** |
| SR 96180 A | −38%** |
| SR 96187 A | −37%* |

Student t test
*p < 0.05
**p < 0.01

Finally, the compounds of formula (II) showed no signs of toxicity at the doses at which they are active.

Consequently, the compounds (II) can be used as drugs in all cases where a cortical cholinergic deficiency is evident, especially for the treatment of degenerative syndromes associated with senescence, and particularly memory disorders and senile dementia.

According to another of its features, the present patent application therefore relates to pharmaceutical compositions in which at least one of the compounds of formula (II) or one of their salts is present as the active ingredient.

In the pharmaceutical compositions of the present invention for oral, sublingual, percutaneous or rectal administration, the active ingredients of formula (II) above can be administered to humans in unit forms of administration, mixed with the conventional pharmaceutical excipients, especially for the treatment of senile dementia. Appropriate unit forms of administration include forms for oral administration, such as tablets, capsules, powders, granules and solutions or suspensions to be taken orally, forms for sublingual and buccal administration, forms for subcutaneous, intramuscular or intravenous administration and forms for rectal administration.

To obtain the desired effect, the dose of active principle can vary between 20 and 500 mg per day.

Each unit dose can contain from 5 to 200 mg of active ingredient in combination with a pharmaceutical excipient. This unit dose can be administered 1 to 4 times a day.

If a solid composition in the form of tablets is prepared, the main active ingredient is mixed with a pharmaceutical vehicle such as gelatin, starch, lactose, magnesium stearate, talc, gym arabic or the like. The tablets can be coated with sucrose or other appropriate substances or they can be treated so as to have a prolonged or delayed activity and so as to release a predetermined amount of active principle continuously.

A preparation in the form of capsules is obtained by mixing the active ingredient with a diluent and pouring the resulting mixture into soft or hard capsules.

Water-dispersible granules or powders can contain the active ingredient mixed with dispersants or wetting agents or with suspending agents such as polyvinylpyrrolidone, as well as with sweeteners or taste correctors.

Rectal administration is effected using suppositories which are prepared with binders melting at the rectal temperature, for example cacao butter or polyethylene glycols.

Parenteral administration is effected using aqueous suspension, isotonic saline solutions or sterile and injectable solutions which contain pharmacologically compatible dispersants and/or wetting agents, examples being propylene glycol and butylene glycol.

The active principle can also be formulated as microcapsules, if appropriate with one or more excipients or additives.

As a pharmaceutical preparation, it is possible to prepare capsules containing:

| | |
|---|---|
| Active principle | 0.010 g |
| Lactose | 0.050 g |
| Magnesium stearate | 0.005 g | by intimately mixing the above ingredients and pouring the mixture into hard capsules.

What is claimed is:

1. A method for treating a pathological condition associated with a cortical cholinergic deficiency, comprising administering to a host suffering from a cortical cholinergic deficiency a 5-alkylpyridazine derivative or a pharmaceutically acceptable salt thereof in an amount effective for cortical cholinergic agonist activity, wherein said 5-alkylpyridazine derivative has the formula $$\text{(II)}$$

in which $R_1$ is a $C_1$–$C_4$ alkyl group or a phenyl group; and $R_2$ and $R_3$, independently are a $C_1$–$C_4$ alkyl group, or $R_2$ and $R_3$, taken with the nitrogen atom to which they are bonded, form a morpholino group.

2. The method according to claim 1, wherein $R_1$ is a $C_1$–$C_4$ alkyl group.

3. The method according to claim 1, wherein $R_1$ is a phenyl group.

4. The method according to claim 1, wherein $R_2$ and $R_3$ independently are a $C_1$–$C_4$ alkyl group.

5. The method according to claim 1, wherein $R_2$ and $R_3$, taken with the nitrogen atom to which they are bonded, form a morpholino group.

6. The method according to claim 1, wherein $R_1$ is $CH_3$ and wherein $R_2$ and $R_3$ independently are $CH_2CH_3$.

7. The method according to claim 1, wherein said pathological condition is a degenerative syndrome associated with senescence.

8. The method according to claim 1, wherein unit doses are administered which contain from 5 to 200 mg of said 5-alkylpyridazine derivative of formula (II) in admixture with a pharmaceutically acceptable excipient.

9. The method according to claim 1, wherein said 5-alkylpyridazine derivative of formula (II) is administered, in admixture with a pharmaceutically acceptable excipient, orally or rectally or by injection.

* * * * *